US008165268B1

(12) United States Patent
Hurd et al.

(10) Patent No.: US 8,165,268 B1
(45) Date of Patent: *Apr. 24, 2012

(54) MATERIAL ANALYSIS BASED ON IMAGING EFFECTIVE ATOMIC NUMBERS

(75) Inventors: Paul J. Hurd, Norfolk, MA (US); Jeff Stillson, Merrimack, NH (US)

(73) Assignee: L-3 Communications Security and Detection Systems, Inc., Woburn, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/847,605

(22) Filed: Jul. 30, 2010

Related U.S. Application Data

(63) Continuation of application No. 12/048,002, filed on Mar. 13, 2008, now Pat. No. 7,769,132.

(60) Provisional application No. 60/894,615, filed on Mar. 13, 2007.

(51) Int. Cl.
*G01N 23/04* (2006.01)
(52) U.S. Cl. ........................................................ 378/57
(58) Field of Classification Search .................. 378/57, 378/62, 42–45, 51, 54, 70, 86–90; 382/132
See application file for complete search history.

(56) References Cited

U.S. PATENT DOCUMENTS

| 5,319,547 | A | 6/1994 | Krug |
|---|---|---|---|
| 5,490,218 | A | 2/1996 | Krug |
| 5,600,700 | A | 2/1997 | Krug |
| 5,642,393 | A | 6/1997 | Krug |
| 5,838,758 | A | 11/1998 | Krug |
| 5,974,111 | A | 10/1999 | Krug |
| 6,041,097 | A | 3/2000 | Roos et al. |
| 6,088,423 | A | 7/2000 | Krug |
| 6,483,893 | B1 | 11/2002 | Achtnig et al. |
| 6,546,072 | B1 | 4/2003 | Chalmers |
| 6,697,663 | B1 | 2/2004 | Lin |
| 7,369,640 | B2 | 5/2008 | Seppi et al. |
| 7,397,886 | B2 | 7/2008 | Avinash et al. |

*Primary Examiner* — Irakli Kiknadze
(74) *Attorney, Agent, or Firm* — Fish & Richardson P.C.

(57) ABSTRACT

Effective atomic numbers associated with pixels in a region are received. An effective atomic number is associated with each pixel in the region. X-ray data for the region is received, and an item within the region is identified from the x-ray data. Some of the pixels in the region are correlated with the item such that the item is associated with an effective atomic number. An image of the region is rendered. The pixels of the item have a display style based on the effective atomic number of the item.

20 Claims, 10 Drawing Sheets

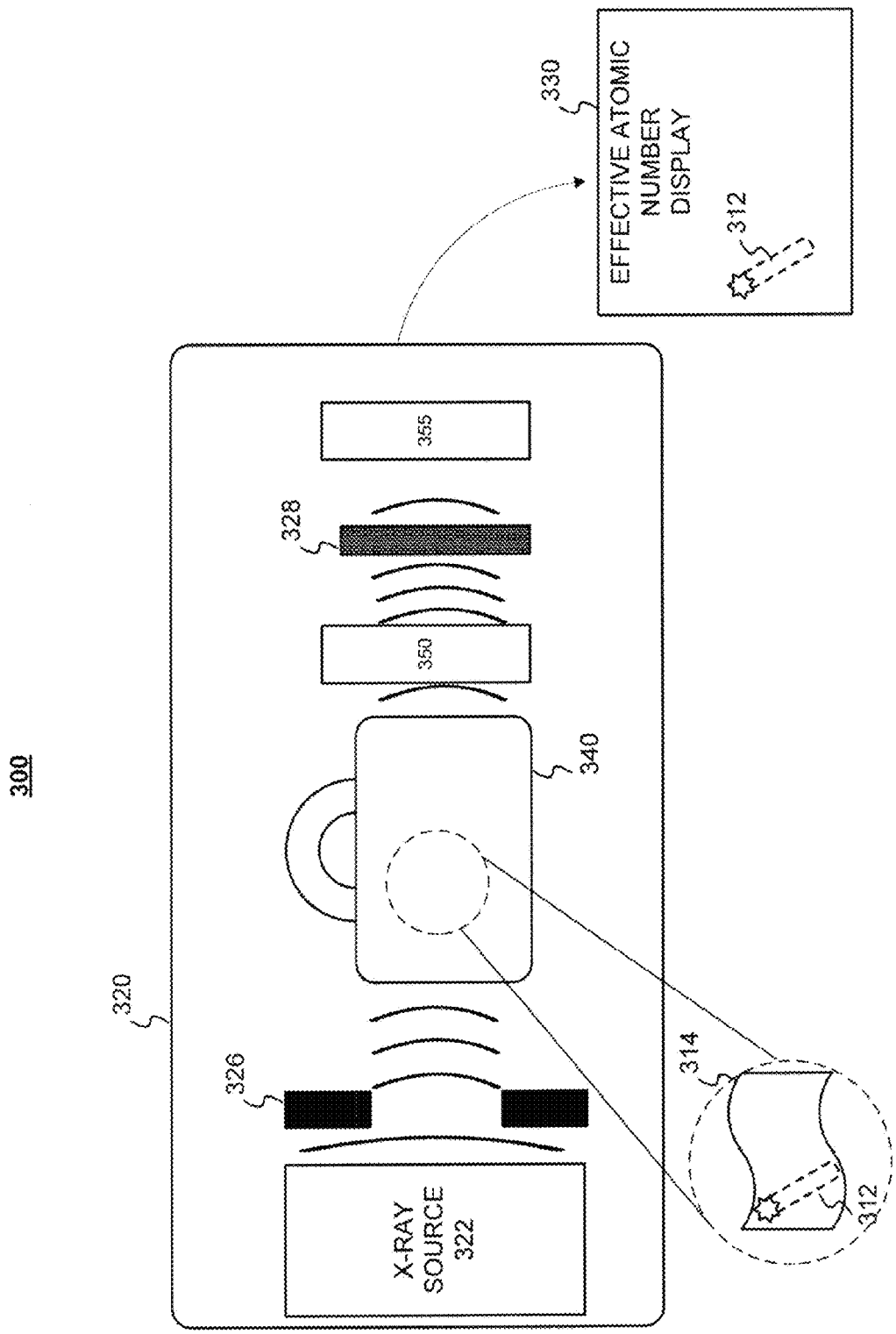

MATERIAL ANALYSIS BASED ON IMAGING EFFECTIVE ATOMIC NUMBERS

CROSS-REFERENCE TO RELATED APPLICATION

This application is a continuation of U.S. patent application Ser. No. 12/048,002, filed Mar. 13, 2008, titled "MATERIAL ANALYSIS BASED ON IMAGING EFFECTIVE ATOMIC NUMBERS," which claims priority from U.S. Provisional Application Ser. No. 60/894,615, titled IMAGING EFFECTIVE ATOMIC NUMBER OF MATERIALS FOR THREAT DETECTION, and filed on Mar. 13, 2007. The contents of the prior applications are incorporated herein by reference in their entirety.

TECHNICAL FIELD

This description relates to analyzing materials based on imaging effective atomic numbers of the materials.

BACKGROUND

Color-coded images representing an average atomic number of objects of interest such as baggage and cargo and items included in these objects may be presented to an operator. The images of the average atomic number generally do not account for the effects of an overlaying or underlaying material around the object of interest.

SUMMARY

In one general aspect, effective atomic numbers associated with pixels in a region are received. An effective atomic number is associated with each pixel in the region. X-ray data for the region is received, and an item within the region is identified from the x-ray data. Some of the pixels in the region are correlated with the item such that the item is associated with an effective atomic number. An image of the region is rendered. The pixels of the item have a display style based on the effective atomic number of the item.

Implementations may include one or more of the following features. An indication of a range of effective atomic numbers of interest may be received. The display style may include color, and a color may be associated with the range of effective atomic numbers of interest. The display style may include one or more patterns, and a pattern is associated with the range of effective atomic numbers of interest. Additional items within the region may be identified from the x-ray data. The additional items may cover the item in a region of overlap, and the additional items may have a effective atomic numbers that are different than the effective atomic number of the item. The effective atomic numbers of the additional items may be within the range of effective atomic numbers of interest, and the additional items and the region of overlap may be represented by the color associated with the range of effective atomic numbers of interest.

In some implementations, receiving an indication of a range of effective atomic numbers of interest may include accessing a predetermined range of effective atomic numbers of interest. A re-sizeable selector that allows selection of one or more ranges of effective atomic numbers of interest may be displayed. The selector may be movable. A size of the selector may correspond to one or more ranges of effective atomic numbers of interest, and a position of the selector may correspond to a mean of the effective atomic numbers included in the range. Identifying an item within the region from the x-ray data may include determining edges within the x-ray data and identifying the item based on the edges. Identifying an item within the region from the x-ray data may include aggregating pixels having similar attenuation values and identifying an item based on one or more boundaries around the aggregated pixels.

In another general implementation, a system of imaging effective atomic numbers includes a processor configured to receive effective atomic numbers associated with pixels in a region. An effective atomic number is associated with each pixel in the region. X-ray data is received for the region, an item is identified within the region from the x-ray data, and some of the pixels in the region are correlated with the item such that the item is associated with an effective atomic number. The system includes a display configured to render an image of the region, where the pixels of the item have a display style based on the effective atomic number of the item.

Implementations may include one or more of the following features. The system may include a source configured to expose an area imaged by the pixels to x-rays of at least two energies. The system may include a sensor to detect x-rays of at least two energies. A filter may be positioned between the area and the sensor, and the filter may separate the x-rays of at least two energies. The display may be a touch screen. An opening may receive an object. The opening may receive cargo and the object may be luggage.

In another general implementation, effective atomic numbers associated with pixels in a region are received. An effective atomic number is associated with each pixel in the region. Penetrating spectral data for the region is received, and an item within the region is identified from the penetrating spectral data. Some of the pixels in the region are correlated with the item such that the item is associated with an effective atomic number. An image of the region is rendered. The pixels of the item have a display style based on the effective atomic number of the item.

Implementations may include one or more of the following features. The penetrating spectral data may include data based on x-rays of at least two energy levels.

Implementations of any of the techniques described above may include a method, a process, a system, a device, an apparatus, or instructions stored on a computer-readable medium. The details of one or more implementations are set forth in the accompanying drawings and the description below. Other features will be apparent from the description and drawings, and from the claims.

DESCRIPTION OF THE DRAWINGS

FIG. 3 shows an example effective atomic number imaging system.

DETAILED DESCRIPTION

Figure 1:
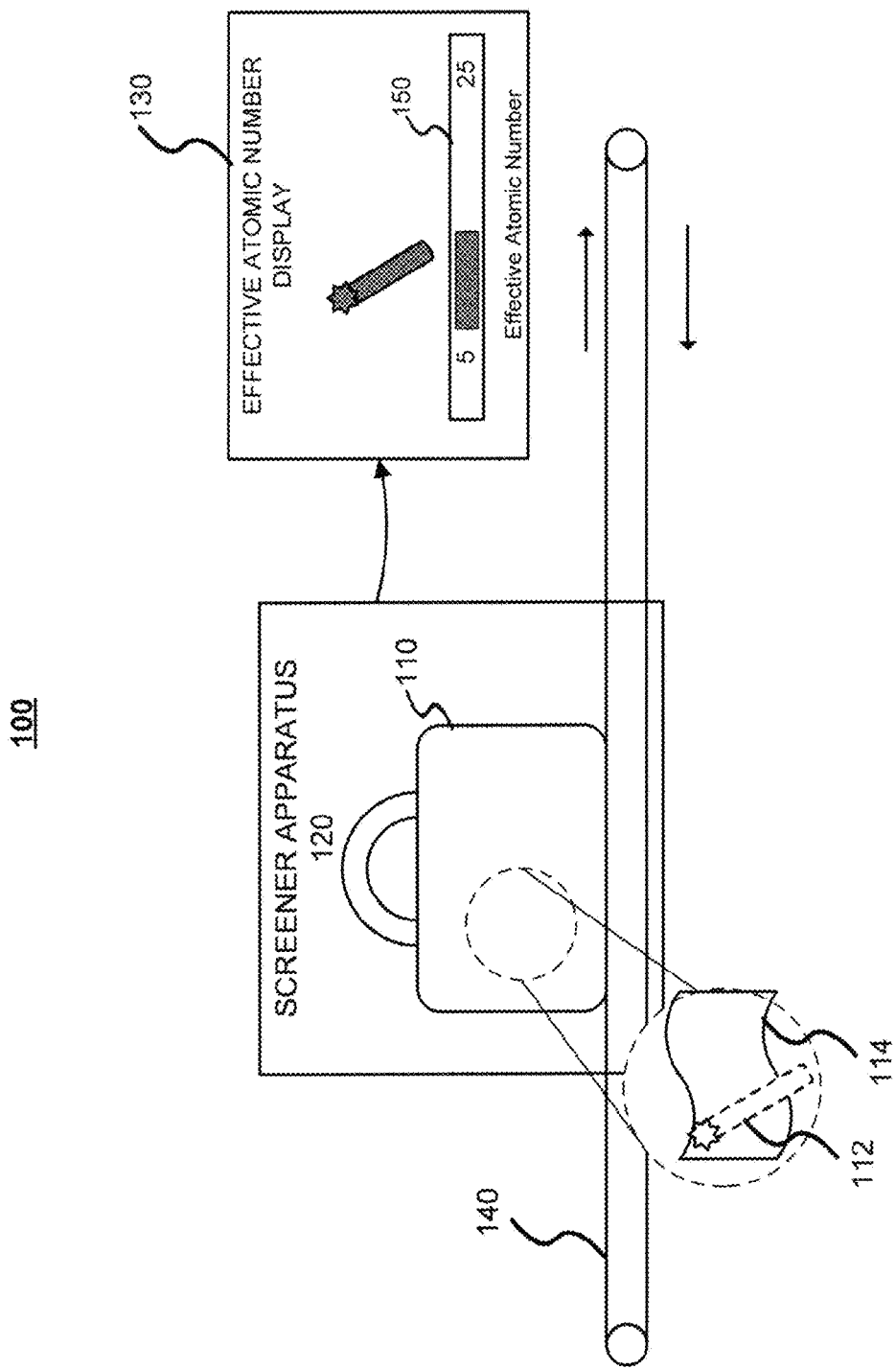
FIG. 1 shows an example of a materials analysis system.

Referring to FIG. 1, an illustration of an example materials analysis system 100 is shown. The system 100 may be, for example, a threat detection system used to determine whether an object of interest (such as a suitcase 110) holds a hazardous, or potentially hazardous, material. For example, the system 100 may be used to determine whether the suitcase 110 holds weapons (such as guns or knives), potentially dangerous items (such as scissors or needles), explosives, or plastic pipe bombs. The system 100 displays an image of the object of interest and items included within the object of interest on an effective atomic number display 130. As discussed in more detail below, the image displayed on the display 130 provides visual separation and differentiation of items based on the effective atomic number of the items, regardless of whether the items overlay or underlay other items having different effective atomic numbers. The image displayed on the display may provide a more accurate representation of the items included in the object of interest as compared to techniques that display an average atomic number of the items and, thus, an image based on effective atomic numbers may allow more accurate identification of the items.

One approach to providing color imaging of cargo and hand carry baggage employs organic-inorganic type imaging with color overlays identifying targeted materials. This type of imaging is generally based on the average atomic number (Z) of the materials without removing the effects of overlying or underlying materials. As such, in many cases, the display of the average atomic number of the materials presents inaccurate information to an operator. For example, an orange color may be associated with an organic material, such as an explosive. However, if the explosive material is covered by a higher atomic number material, such as a sheet of metal, the explosive no longer shows on the display as an orange organic object. Instead, the explosive is shown with a color associated with the atomic number of the metal sheet of metal. As a result, the display of the average atomic number gives the operator a false impression that the explosive material is not a potential threat. One technique to mitigate this effect is the use of "operator assist" techniques in which, for example, red bounding boxes (which may be called threat boxes) may be used to identify a targeted material. However, display of red bounding boxes may be disfavored because such techniques are believed to distract the operator from the function of finding weapons. In particular, the red bounding boxes may confuse and distract the operator. In general, the overall performance of such "operator assist" techniques results in relatively low detection and high false alarm rates. Detection rate is generally the number of correct detections (e.g., a determination that a hazardous item is present when a hazardous item is in fact present) made over a period of time, and false alarm rate is the number of incorrect detections (e.g., a determination that a hazardous item is present when a hazardous item is not actually present) made over a period of time.

However, the display 130 displays an image in a true effective atomic number color space as opposed to an average atomic number color space. In other words, the image shown by the display 130 may be used to differentiate and separate items according to effective atomic number. Such an image may provide the operator with a more accurate representation of the suitcase 110 and the contents of the suitcase 110.

The system 100 includes a screener apparatus 120 through which the suitcase 120 passes. The screener 120 exposes the suitcase 110 to x-ray radiation having at least two energy levels, and the screener 120 senses x-ray radiation that passes through the suitcase 110. The effective atomic number of the materials of the suitcase 110 and the materials of any items within the suitcase 110 may be determined by exposing the material to x-rays of two of more different energies and analyzing the absorption of the x-rays by the materials at the different energies. The effective atomic number is a material-specific property, and the effective atomic number may be referred to as the true Z number. Briefly, materials that readily absorb x-rays, such as metals, tend to have relatively high effective atomic numbers (e.g., above 20). These materials absorb both lower-energy x-rays and higher-energy x-rays. Materials that absorb x-rays less readily, such as organic materials and plastics, tend to have lower effective atomic numbers (e.g., between 5 and 12). These materials tend to absorb fewer low energy x-rays as compared to materials having a higher effective atomic number. Organic materials may include items such as food and clothing, and inorganic materials may include items made from materials such as metal In particular, characteristic differences in photoelectric effect scattering and Compton scattering, and comparison of the pairwise differential attenuation of the higher energy x-rays and the lower energy x-rays may be used to determine whether differences in attenuation may be attributed to the presence of a specific material regardless of whether the material is overlayed (e.g., covered) or underlayed by a different material of a different atomic number. Techniques for determining the effective atomic number may be found in commonly owned U.S. Pat. Nos. 5,319,547, 5,600,700, 5,642,393, and 6,088,423, all of which are hereby incorporated by reference in its entirety.

The items in the image shown on the display 130 are each associated with one or more display styles. Each display style indicates an effective atomic number of a material from which the items are composed. The display style may be a particular color. For example, items having an effective atomic number between five and ten, such items including organic material, may be colored orange, and items having an effective atomic number between seventeen and twenty-two, such as items including metallic material, may be colored blue. Items within the suitcase 110 may overlay or underlay each other. For example, the suitcase 110 may include a first item having an effective atomic number of five and a second item having an effective atomic number of twenty-one. The first item may overlay the second item if the first item covers, or partially covers, the second item. The first item may underlay an item if the first item is covered, or partially covered, by the second item. A region of overlap occurs at the overlay or the underlay. Rather than displaying the average atomic number of the first and second item at the region of overlap, the display 130 may display an image in which the first and second item with the region of overlap colored based on a received atomic number of interest or a range of atomic numbers of interest. In some implementations, the display style may include shading and/or cross-hatching in addition to, or instead of, color. In some implementations, the display style may include a texture.

Figure 2A:
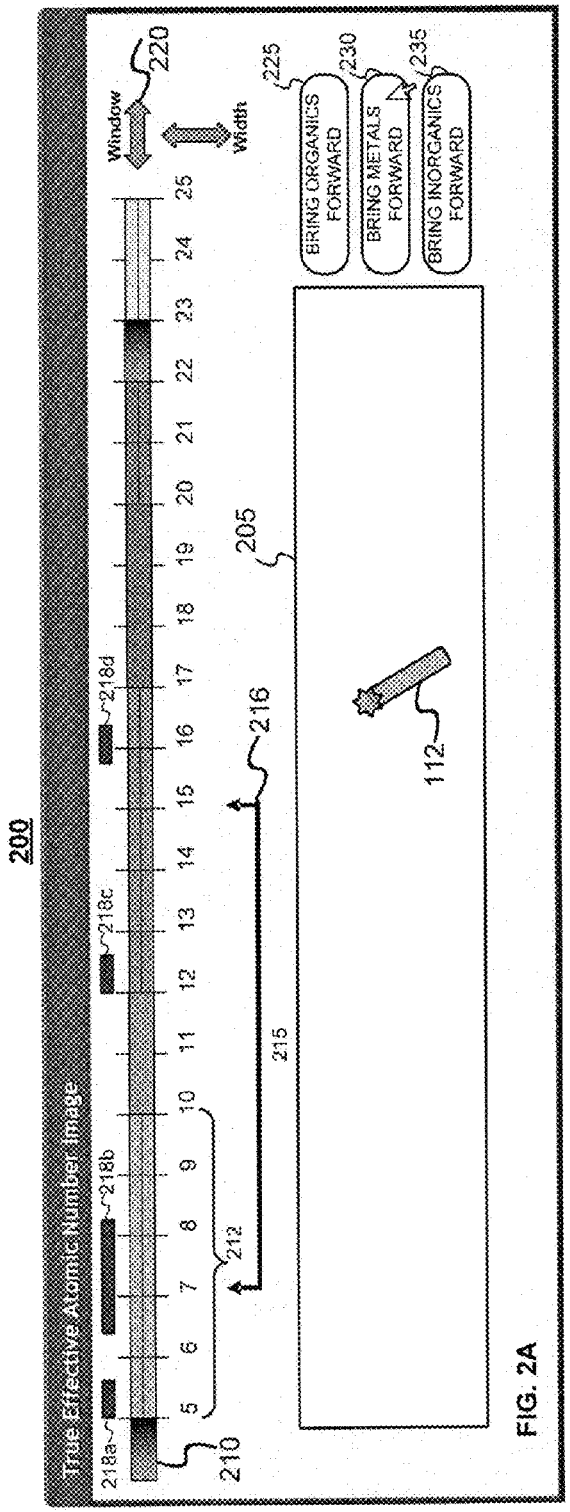
FIGS. 2A and 2B show an example interface for interacting with an image representing effective atomic numbers.
Figure 2B:
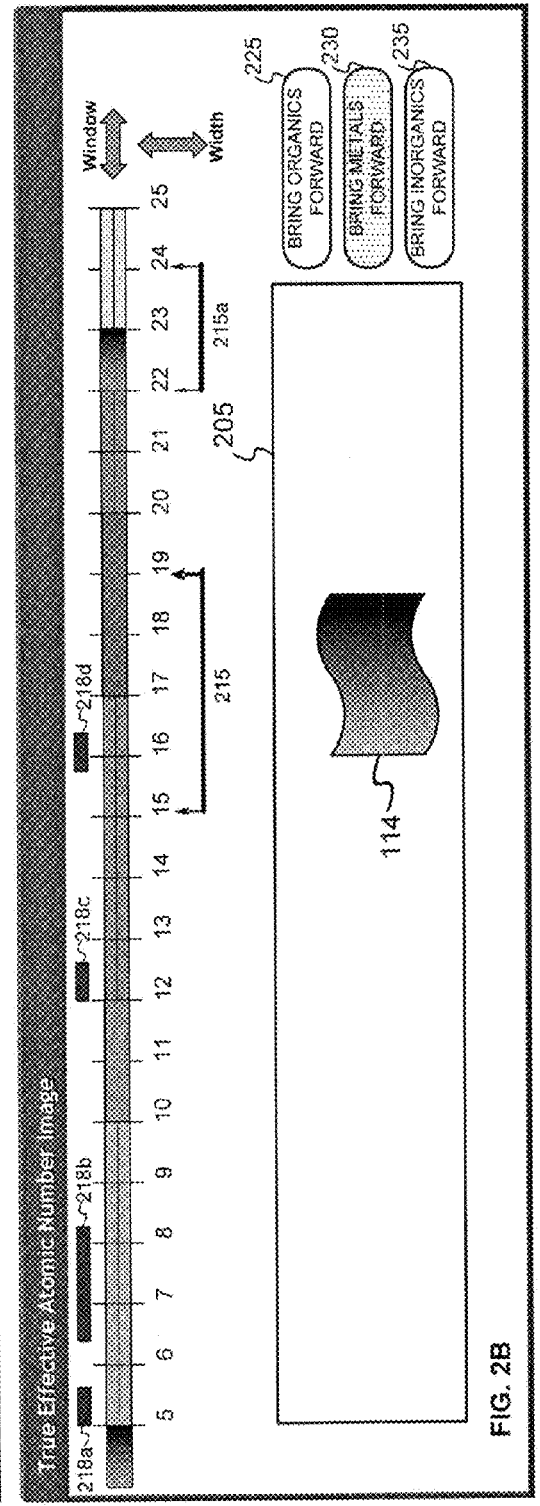

In some implementations, the display 130 also may display a selector 150 that allows a selection of one or more ranges of effective atomic numbers to include in the color-coded image shown on the display 130. In the example shown, a plastic pipe bomb 112 is covered by a sheet of metal 114. However, the color-coded image shown on the display 130 shows only the plastic pipe bomb 112 because the setting of the selector 150 specifies that materials having effective atomic numbers similar to that of the sheet of metal 114 be excluded from the color-coded image. In some implementations, materials having effective atomic numbers similar to that of the sheet of metal 114 are not excluded from the color-coded image. For example, both the sheet of metal 114 and the plastic pipe bomb 112 are shown, and any overlap region between the sheet of metal 114 and the plastic pipe bomb 112 is colored according to an indicated effective atomic number of interest. Although specific examples are discussed below, the effective atomic number display 130 may display effective atomic number information derived from any type of dual energy x-ray system Additionally, as shown in FIGS. 2A and 2B, in some implementations, an interface shown on the display 130 may allow the operator to select one or more ranges of effective atomic numbers to include in the image. Thus, selecting a range may allow the operator to view only items that have effective atomic numbers associated with explosives. In some implementations, selecting a range of effective atomic numbers may result in items that have effective atomic numbers associated with explosives moved to the foreground, or otherwise emphasized, but other items with different effective atomic numbers are still shown in the image. As a result, the bounding boxes discussed above may not be necessary because the operator may be able to discern objects based on the more accurate representation of the objects themselves in the image without using operator assist techniques (such as red bounding boxes drawn around potential objects of interest) to draw the operator's attention to the object. Displaying the image in true effective atomic number space may result in a higher probability of detection and a lower false alarm rate as compared to implementations that use red bounding boxes to highlight potential objects of interest.

In addition to providing an image based on effective atomic number, the display 130 also allows a user to select one or more ranges of effective atomic numbers to include in the displayed image. The one or more ranges of effective atomic numbers may be selected using the selector 150. For example, an operator of the system 100 may select the range of effective atomic numbers using the selector 150. In some implementations, the ranges are preset ranges that may be set by, for example, the manufacturer. In some implementations, the ranges are set by a supervisor and cannot be modified by others.

As discussed in more detail below, selection of the ranges allows an item made of a particular material with an effective atomic number within the range to be shown on the foreground of the image even if the item is covered by, or rests on top of, items composed of another material. For example, a plastic explosive 112 enclosed in the suitcase 110 and covered by a sheet of metal 114 appears without being obstructed by the sheet of metal 114 when the selection of the range of effective atomic numbers to include in the image includes the effective atomic number of the plastic explosive 112 but the selected range does not include the effective atomic number of the sheet of metal 114. As discussed with respect to FIGS. 2A-2H and FIGS. 6A-6C, the color-coded image displayed on the display 130 is a color image in effective atomic number space, where each color represents a particular effective atomic number or a range of effective atomic numbers. Displaying the image in effective atomic number space allows a particular item that includes a particular material to be displayed without interference from nearby overlaying or underlying items made from different materials having distinct effective atomic numbers.

In the example shown in FIG. 1 the suitcase 110 includes a plastic pipe bomb 112 filed with a plastic explosive covered by a sheet of metal 114. The suitcase 110 is placed on a conveyor belt 140 and moved into the screener 120. In the screener 120, the suitcase 110 is exposed to x-ray radiation having at least two energies. An image of the effective atomic number of the suitcase 110 and the items within the suitcase 110 is displayed on the display 130. The settings of the display 130 are such that materials having effective atomic numbers similar to that of the plastic pipe bomb 112 are shown on the display 130 and items having effective atomic numbers similar to that of the sheet of metal 114 are not shown. In other examples, the settings of the display 130 may be such that the plastic pipe bomb 112 and the sheet of metal 114 are shown. The portions of the plastic pipe bomb 112 and the sheet of metal 114 that overlap may be color-coded to correspond to an effective atomic number of interest.

Although the example shown in FIG. 1 relates to the screening of the suitcase 110, in other examples, a system similar to the system 100 may be used to screen items of interest other than the suitcase 110. For example, items of interest that are larger than the suitcase 110, such as shipping containers carried on cargo ships and/or trains, trucks, and/or automobiles, may be scanned. In these examples, the screener 120 may be made larger in order to accommodate larger sized objects. In other examples, smaller objects, such as purses, packages, parcels, and/or briefcases, may be screened. The example system 100 discussed with respect to FIG. 1 may be used, for example, at an airport. In other examples, threat detection systems similar to the system 100 may be used at seaports, border crossings, and/or public gathering places.

Additionally, although the system 100 may be used as a threat detection system, in some implementations, the system 100 may be used to analyze materials for contaminants and/or inhomogenities. For example, contaminants and/or inhomogenities may have different effective atomic numbers than the materials in which the contaminants and/or inhomogenities are included. Thus, the contaminants and/or inhomogenities may be identified through the effective atomic number display 130.

Referring to FIGS. 2A and 2B, an example interface 200 is shown. The example interface may be shown on a display configured to display a color-coded image of an object of interest in effective atomic number space, such as the display 130 discussed above with respect to FIG. 1. In some implementations, the interface 200 is presented to an operator of a threat detection system, and the interface 200 assists the operator in determining whether objects examined by the threat detection system include hazardous, or potentially hazardous, materials. The interface 200 may be used to view an image generated from data received from a screener, such as the screener 120 discussed above with respect to FIG. 1. In the examples shown in FIGS. 2A and 2B, an image 205 shows items included in the suitcase 110. In particular, FIG. 2A shows the image 205 with a first window of effective atomic numbers selected for inclusion in the image 205, and FIG. 2B shows the image 205 with a second window of effective atomic numbers selected for inclusion in the image 205.

The image 205 is a color-coded true effective atomic number image that represents the effective atomic number for materials shown in the image 205 with a particular color according to a legend 210. For example, materials having an atomic number of five to ten are colored orange as shown in portion 212 of the legend 210. A selector 215 indicates a window 220 of effective atomic numbers that are imaged in the image 205. The selector 215 corresponds with the effective atomic numbers shown on the legend 210, and the selector 215 may be placed near the legend 210 for the convenience of the operator. In the example shown in FIG. 2A, the selector 215 indicates that the window 220 of effective atomic numbers to include in the image 205 is seven to fifteen. As a result, the image 205 includes the plastic pipe bomb 112 enclosed in the suitcase 110 discussed in FIG. 1. However, the image 205 does not include the sheet of metal 114, which covers the plastic pipe bomb 112, because the effective atomic number of the sheet of metal 114 is greater than fifteen.

A size of the selector 215 determines a range of effective atomic numbers to include in the image 205, and a position of the selector 215 determines a mean effective atomic number of the range of effective atomic numbers. For example, making the selector 215 larger selects a larger range of effective atomic numbers for inclusion in the image 205, and making the selector 215 smaller selects a smaller range of effective atomic numbers for inclusion in the image 205. In some implementations, the selector 215 may be made larger or smaller by increasing or decreasing, respectively, the length of the selector 215. For example, a side 216 of the selector 215 may be highlighted with a mouse, or other input device, and dragged to make the selector 215 longer. In some implementations, the image 205 may be displayed on a touch screen device, and the size of the selector 215 may be increased or decreased by the operator touching the selector 215 and manually re-sizing the selector 215. In some implementations, the selector 215 may be re-sized automatically based on data received from an automated process or a machine rather than from input received from an operator.

A position of the selector 215 determines the mean of the range of effective atomic numbers included in the window 220. For example, the center of the selector 215 may be located at a mid-point of the window 220 with respect to the legend 210. The mid-point of the window 220 may be the mean value of the effective atomic numbers included in the window 220. In the example shown in FIG. 1, the center of the selector 215 is located at an atomic number of eleven according to the legend 210. The selector 215 may be re-positioned by, for example, placing a mouse pointer, or some other input device, at the center of the selector 215 and dragging the entire selector 215 such that the center of the selector 215 moves to a desired effective atomic number. In some implementations, the image 205 may be displayed on a touch screen. In these implementations, the selector 215 may be repositioned by the operator touching the screen where the selector 215 is shown and dragging the selector 215 such that the selector 215 is centered on the effective atomic number of interest according to the legend 210. In some implementations, the selector 215 may be re-positioned automatically based on data received from an automated process or a machine rather than from input received from an operator.

The interface 200 also includes bands 218a, 218b, 218c, and 218d that indicate ranges of effective atomic numbers included in the image 205 regardless of whether the ranges are selected by, for example, the selector tool 215. The effective atomic numbers included in the bands 218a, 218b, 218c, and 218d may be effective atomic numbers of a set of explosives, or of a product of interest. Although four bands are shown in the examples of FIGS. 2A and 2B, other examples may include more or fewer bands.

Referring to FIG. 2B, the image 205 may updated in response to a change in the window 220 of effective atomic numbers selected to be included in the image 205. In particular, the change in the window 120 results in materials having higher effective atomic numbers being included in the image 205 and materials having lower effective atomic numbers being excluded from the image 205. Thus, the sheet of metal 114 is shown in the image 205 after the updating of the window 120, but the plastic pipe bomb 112 is not shown.

The window 120 of effective atomic numbers is changed by re-sizing and repositioning the selector 215. In particular, as compared to FIG. 2A, the selector 215 shown in FIG. 2B has been re-sized and repositioned such that the image 205 includes representations of materials having effective atomic numbers between fifteen and nineteen. Additionally, an additional selector 215a has been added. The additional selector 215a allows selection of a second window 120 of effective atomic numbers for inclusion in the image 205. In the example shown in FIG. 2B, the additional selector 215a indicates that materials having effective atomic numbers between twenty-two and twenty-four are also to be included in the image 205. In this example, the piece of metal 114 is shown colored in a gray gradient. Although two selectors 215 and 215a are shown in this example, in other examples more than two selectors may be used. Using multiple selectors allows finer selection of effective atomic numbers, which may allow an operator to visualize materials having effective atomic numbers in several particular narrow bands of effective atomic numbers of interest that correspond to different types of hazardous, or potentially hazardous materials.

Referring again to FIG. 2A, in some implementations, the interface 200 may include selectable controls 225, 230, and 235 that allow certain types of materials to be included in the image 205. In the example shown, selection of the control "BRING ORGANICS FORWARD" 225 brings organic materials to the foreground of the image 205, selection of the control "BRING METALS FORWARD" 230 brings metal materials to the foreground of the image 205, and selection of the control "BRING INORGANICS FORWARD" 235 brings inorganic materials to the foreground of the image 205. In the example shown, the control 230 is selected in order to bring metal materials to the foreground of the image 205. As a result of the selection of the control 230 and/or the resizing of the selector 215, the image 205 is updated to show the sheet of metal 112 in the foreground, as shown in FIG. 2B. The controls 225, 230, and 235 may be selected by an operator using an input device, such as a mouse, stylus, or touch screen. In some implementations, the controls 225, 230, and 235 may be selected from the output of an automated process or a machine.

Figure 2C:
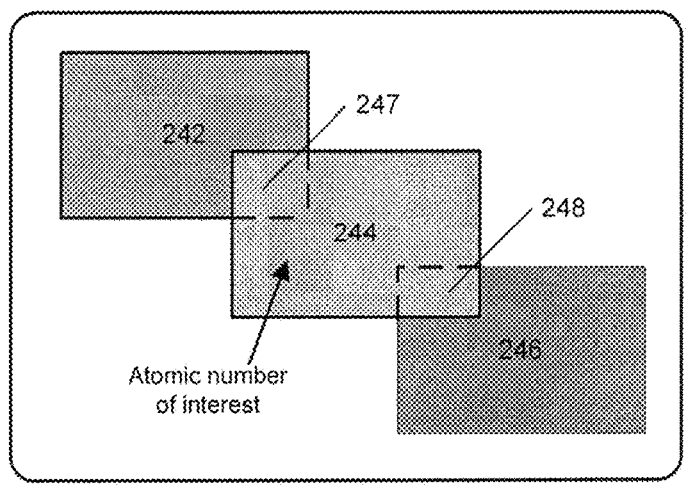
FIGS. 2C-2H show illustrations of image of items that are color-coded based on effective atomic numbers of the items is shown.
Figure 2D:
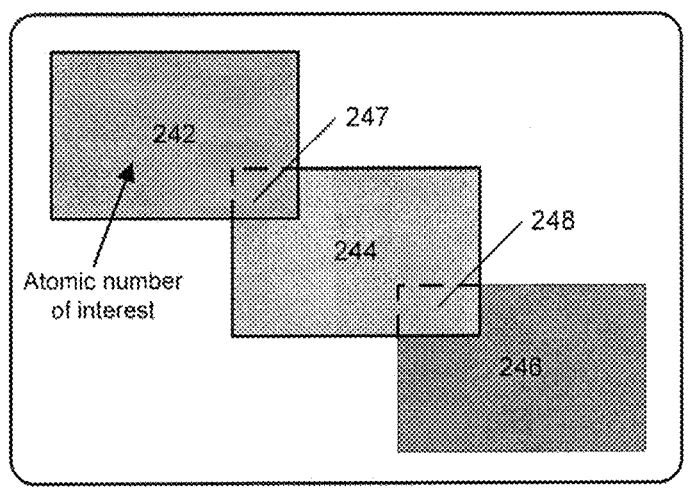
Figure 2E:
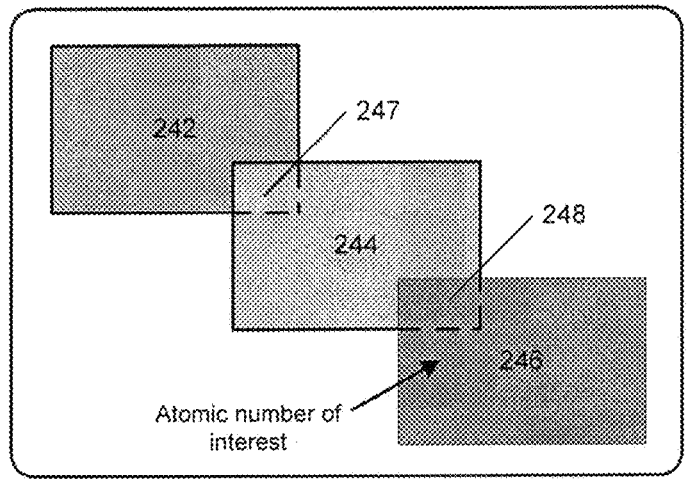

Referring to FIGS. 2C-2E, an illustration of an image of items that are color-coded based on effective atomic numbers of the items is shown. An item 242 has an effective atomic number that is color-coded as green, an item 244 has an effective atomic number that is color-coded as orange, and an item 246 has an effective atomic number that is color-coded as blue. The items 242, 244, and 246 have different effective atomic numbers. For example, the item 242 may be composed of an inorganic material with an effective atomic number of nine, the item 244 may be composed of an organic material with an effective atomic number of seven, and the item 246 may be composed of a metal material with an effective atomic number of twenty-two. The item 242 overlaps the item 244 at an overlap region 247, and the item 244 overlaps the item 246 at an overlap region 248. Rather than displaying a color representing an average or a composite of the effective atomic numbers (such as the average atomic number) associated with the items 242 and 244 in the overlap region 247, the color associated with effective atomic number of the item having an effective atomic number of interest is shown in the overlap region 247. As discussed above, an effective atomic number of interest, or a range of effective atomic numbers of interest, may be, for example, selected by an operator or may be pre-configured values.

Referring to FIG. 2C, the item 242 has an effective atomic number that matches or is within a range of effective atomic numbers of interest. As a result, the regions of overlap 247 and 248 are color-coded orange. As a result, the entire item 244 may be discerned, which may help identify the item 244. Referring to FIG. 2D, the item 242 has an effective atomic number of interest that matches an effective atomic number of interest or is within a range of effective atomic numbers of interest. The region of overlap 247 is also color-coded green. Referring to FIG. 2E, the item 246 has an effective atomic number that matches an effective atomic number of interest or is within a range of effective atomic numbers of interest, and the region of overlap 248 is color-coded to match the item 246.

Figure 2F:
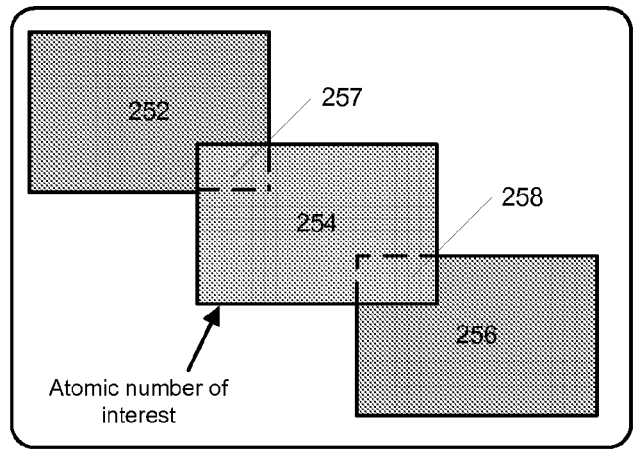
Figure 2G:
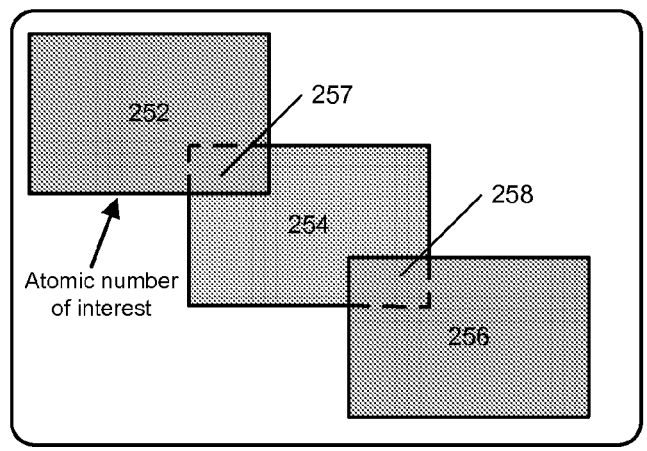

Referring to FIGS. 2F and 2G, another illustration of an image of items that are color-coded based on effective atomic numbers of the items is shown. In this example, items 252 and 256 both have effective atomic numbers that are color-coded green. For example, the items 252 and 256 may both be inorganic materials. The item 254 has a different effective atomic number than items 252 and 256. The item 254 may be, for example, an organic material, and is this example, the item 254 is color-coded orange. The item 252 and the item 254 overlap at a region of overlap 257, and the item 254 and the item 256 overlap at a region of overlap 258. In the example shown in FIG. 2F, the effective atomic number of interest includes the effective number of the item 254, and the regions of overlap 257 and 258 are color-coded orange to match the item 254. In the example shown in FIG. 2G, the effective atomic number of interest includes the effective atomic numbers of the item 252 and the item 256, and the regions of overlap 257 and 258 are both color-coded green to match the items 252 and 256.

Figure 2H:
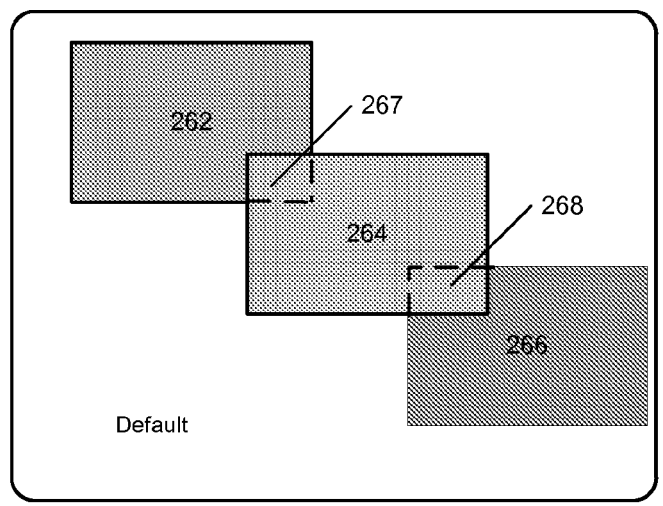

Referring to FIG. 2H, an illustration of an image of items that are color-coded based on default settings for effective atomic number is shown. The default settings indicate a preferential order in which to display items according to an effective atomic number associated with the items. In the example shown, organic materials with a lower effective atomic number (such as an item 264) have preference over inorganic materials with a mid-range effective atomic number (such as an item 262) and metallic materials with a higher effective atomic number (such as an item 266). In this example, the item 262 is color-coded green, the item 264 is color-coded orange, and the item 266 is color-coded blue. The inorganic item 262 and the organic item 264 overlap at a region of overlap 267, and the organic item 264 and the metallic item 266 overlap at a region of overlap 266. Thus, because the default settings specify that organic materials have a preference over inorganic materials and metallic materials, the regions of overlap 267 and 268 are color-coded the same as the organic item 264. This is in contrast to techniques that show an average or composite of the atomic numbers of the items 262 and 264 in the region of overlap 267, and an overage or composite of the items 264 and 266 in the region of overlap 268. In some implementations, an automated process may be weighted towards organics such that organic items, such as the organic item 264 are colored regardless of the composition of the background in which the item is located. As a result, the image shows the entire organic item 264, which may aid in the identification of the organic item 264. Although in the example shown, the default settings specify that organic materials have a preference over inorganic and metallic materials, in other examples, different orderings are possible.

Referring to FIG. 3, an example effective atomic number imaging system 300 is shown. The system 300 may be similar to the system 100 discussed above with respect to FIG. 1. The system 300 includes a screening system 320 and a display 330 for imaging effective atomic numbers of screened materials. The screening system 320 may be similar to the screener 320 discussed and the display 330 may be similar to the display 130, both of which are discussed above with respect to FIG. 1.

The screening system 320 includes an x-ray source 322, a first detector 350 and a second detector 355. The screening system 320 also may include a collimator 326 and a filter 328. The x-ray source 322 exposes an object of interest 340 to x-ray radiation of at least two energy levels. The x-rays may be collimated by the collimator 326, which may be made of lead or another material of sufficient thickness to block the x-rays. The collimated x-rays pass through the object 340, are attenuated by the object 340 and the contents of the object 340, and the attenuated x-rays are sensed by the first detector 350. The first detector 350 may be, for example, a scintillator, and the x-rays may pass through the first detector 350. The filter 328 may be placed in front of the second detector 355 such that only x-rays having energies below a cut-off energy of the filter 328 reach the second detector 355. The filter 328 may be made from a metal material such as, for example, copper. The arrangement of the first and second detectors shown in the example of FIG. 3 may be referred to as a front-to-back configuration. In a front-to-back configuration, the detectors 350 and 355 image the same area, thus data collected by the detectors 350 and 350 generally is aligned at the time of detection without further correction. In some implementations, the first detector 350 and the second detector 355 may be placed next to each other in a side-by-side configuration.

Thus, the first and second detectors sense attenuated x-rays of different energy levels, with the second detector sensing the attenuation of the higher energy x-rays. The attenuation of the lower and higher energy x-rays may be compared such that the effective atomic number of the material of the suitcase and the materials of items within the object 340 is determined. For example, an attenuation measurement may be taken for each pixel (which corresponds to a portion of the object 340) to determine how much attenuation of the x-rays the object 340 caused. The attenuation values may be determined from a ratio of the intensity of the detected x-ray energy to the intensity of the initial x-ray energy from the x-ray source 322. Attenuation pairs (e.g., attenuation of the higher energy x-ray and attenuation of the lower energy x-ray) are determined for the pixels over the exposed region of the object 340. The attenuation pairs are compared to attenuation values of nearby pixels to determine whether differences in attenuation between nearby pixels is attributable to the presence of a specific material. In this manner, an estimate of the effective atomic number of the material may be determined, even if the material is overlayed or underlayed by materials having a different atomic number. In the example shown in FIG. 3, a plastic pipe bomb 312 is overlayed by a sheet of metal 314. For example, the plastic pipe bomb 312 may overlay the sheet of metal 314 if the plastic pipe bomb 312 is further from the first detector 350 than the sheet of metal 314. The effective atomic number may be contrasted to the average atomic number. Continuing the above example, the average atomic number is the average of the effective atomic number of the material of the object 340 and all of the materials of all of the items included in the object 340. In comparison, the effective atomic number is the atomic number of each of the materials within the object 340, and the effective atomic number is a unique characteristic of each material.

The system 300 also includes the display 330, which displays the effective atomic number determined as discussed above. The display 330 also displays an interface that allows the effective atomic numbers included in the displayed image to be varied, such as the interface 200 discussed above with respect to FIGS. 2A and 2B. In the example shown, the effective atomic numbers included in the displayed image include an effective atomic number of the plastic pipe bomb 314. Thus, the plastic pipe bomb 314 is shown on the display 330.

Figure 4:
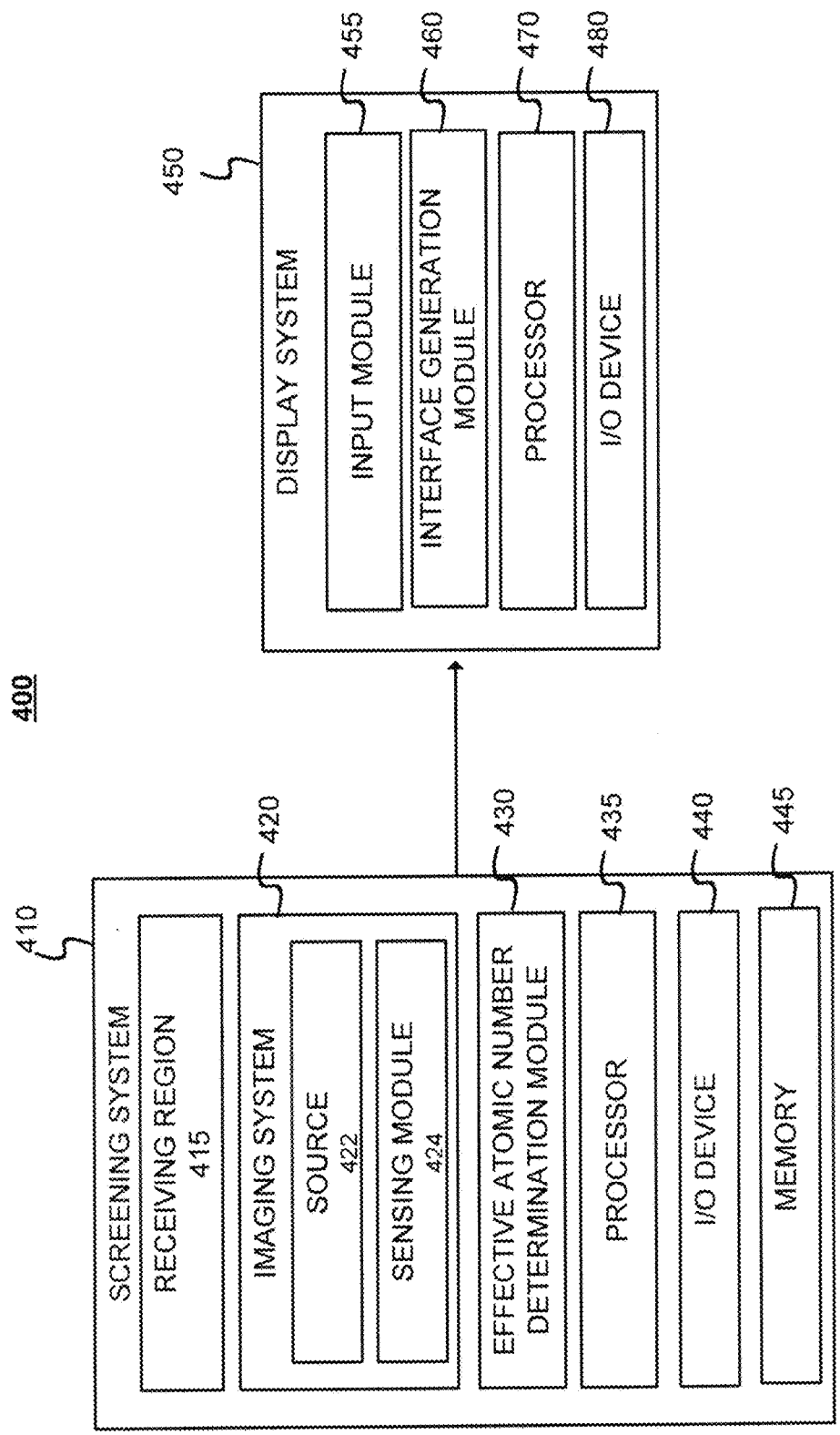
FIG. 4 shows an example system for imaging effective atomic numbers.

Referring to FIG. 4, a block diagram of an example effective atomic number imaging system 400 is shown. The system 400 includes a screening system 410 and a display system 450 that receives and displays data from the screening system 410 as an image in effective atomic number space.

The screening system 410 may be used to screen objects to determine whether the object includes materials of interest. In particular, the screening system 410 determines an effective atomic number of materials on an in the object and outputs the effective atomic number of the materials to the display system 430. The screening system 410 includes a receiving region 415 that is configured to receive an object to be screened, an imaging system 420, an effective atomic number determination module 430, a processor 435, and an input/output device 440.

The receiving region 415 is appropriately sized depending on the object to be screened. For example, the receiving region 415 may be large enough to receive a suitcase or other luggage item. In other examples, the receiving region 415 may accommodate a truck or shipping container. In other examples, the screening system 410 may be used to detect inhomogeneities and/or contaminants in, for example, processed food items such as cereals. In this example, the receiving region 415 may be sized to fit around a conveyor belt in a food processing plant.

The screening system 410 also includes the imaging system 420, which includes a source 422 and a sensing module 424. The source 422 may be a source that emits x-rays of at least two energies, and the source 422 may be similar to the x-ray source 322 discussed above with respect to FIG. 3. The sensing module 424 includes detectors to sense x-rays that are produced by the source 422. The sensing module 424 may include a filter such that the detectors included in the sensing module 424 sense either higher energy x-rays or lower energy x-rays. The effective atomic number determination module 430 determines the effective atomic number of the materials through which the x-rays generated by the x-ray source 422 pass. The module 430 may use the detected attenuated x-rays to determine the effective atomic numbers as discussed above with respect to FIG. 3. In the example shown in FIG. 4, the effective atomic number determination module 430 is shown as a component of the screening system 410, this is not necessarily the case. In other examples, the module 430 may be implemented as component separate from, and in communication with, the screening system 410.

The screening system 410 also includes the processor 435, the input/output device 440, and the memory 445. The memory 445 stores instructions that, when executed by the processor 435, cause the effective atomic number module 430 to perform operations such as determining the effective atomic number of materials include in the object of interest based on the sensed attenuated x-rays. The memory 445 also may store data sensed by the sensor module 420 and instructions for retrieving the data from the sensor module 420. The memory 445 may be any type of computer-readable medium. The processor 435 may be a processor suitable for the execution of a computer program such as a general or special purpose microprocessor, and any one or more processors of any kind of digital computer. Generally, a processor receives instructions and data from a read-only memory or a random access memory or both. The processor 435 receives instruction and data from the components of the screening system 410, such as, for example, the imaging system 420 and/or the effective atomic number determination module 430, to, for example, analyze data from the imaging system 420 to determine effective atomic numbers. In some implementations, the screening system 410 includes more than one processor. The input/output device 445 may be any device able to transmit data to, and receive data from, the screening system 410. For example, the input/output device 445 may be a mouse, a touch screen, a stylus, a keyboard, or any other device that enables a user to interact with the screening system 410. In some implementations, the input/output device 445 may be configured to receive an input from an automated process or a machine.

The display system 450 includes an input module 455, an interface generation module 460, a processor 470, and an input/output device 480. The input module 455 receives effective atomic number information from the screening system 410 or the effective atomic number determination module 420. The interface generation module 460 displays an image in effective atomic number space of the object screened by the screening system 410. The interface generation module 460 also generates and displays an interface that allows interaction with the displayed image. The interface may be similar to the interface discussed above with respect to FIGS. 2A and 2B.

The display system 450 also includes a processor 470 and an input/output device 480. The processor 470 executes instructions that cause the interface generation module 460 to generate and display the interface and process commands received from the input/output device 480. The input/output device 480 may be any device that allows a user to interact with the display system 450. For example, the input/output device 480 may be a mouse, a keyboard, or a touch screen.

Figure 5:
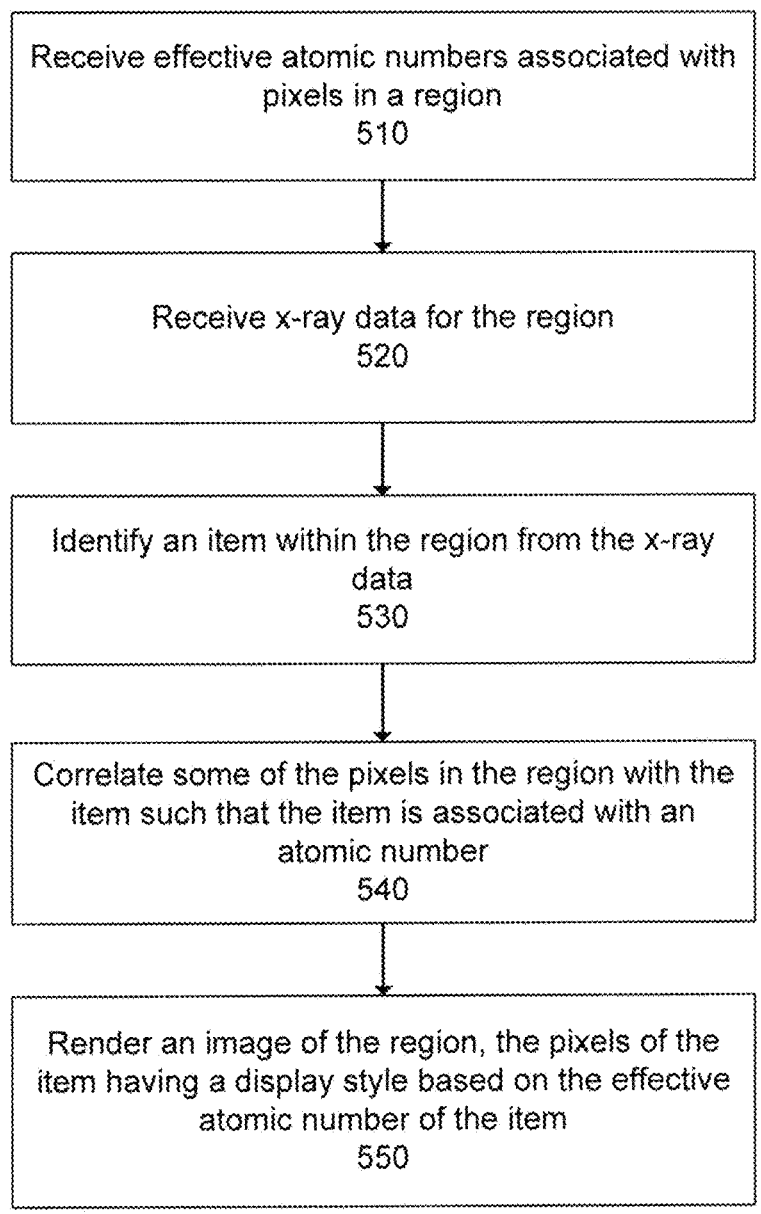
FIG. 5 shows an example process for imaging effective atomic numbers of materials.

Referring to FIG. 5, an example process 500 for imaging effective atomic numbers of materials is shown. The process 500 may be performed by, for example, one or more processors included in a system such as the system 400 discussed above with respect to FIG. 4. In some implementations, the process 500 may be performed by the display system 450.

Effective atomic numbers associated with pixels in a region are received (510). An effective atomic number is associated with a pixel in the region. In some implementations, the region is a representation of an area imaged by an imaging system. For example, the region may represent an image of a physical area that includes an object of interest, such as a suitcase that may contain explosives. In other examples, the region may be a portion of a physical area that includes an object of interest.

In implementations in which the region is exposed to x-rays of two energies, a higher-energy x-ray and a lower-energy x-ray, the effective atomic numbers associated with the pixels in the region may be determined as follows. The attenuation of the lower and higher energy x-rays may be compared such that the effective atomic number of the material of the suitcase and the materials of items within the object of interest is determined. For example, an attenuation measurement may be taken for each pixel (which images a portion of the physical area that includes the object of interest) to determine how much attenuation of the x-rays the object of interest caused. The attenuation values may be determined from a ratio of the intensity of the detected x-ray energy to the intensity of the initial x-ray energy from the x-ray source. Attenuation pairs (e.g., attenuation of the higher energy x-ray and attenuation of the lower energy x-ray) are determined for the pixels in the region. The attenuation pairs are compared to attenuation values of nearby pixels to determine whether differences in attenuation between nearby pixels is attributable to the presence of a specific material. In this manner, an estimate of the effective atomic number of the material may be determined for each pixel, even if the material is overlayed or underlayed by materials having a different atomic number.

X-ray data is received for the region (520). The x-ray data may be the higher-energy x-ray energy and/or the lower-energy x-ray energy. An item within the region is identified using the x-ray data (530). Continuing the example above, the item may be an image of an item in the suitcase. For example, the item may be a metal weapon or a plastic object. The item may be identified using the x-ray data by, for example, applying an edge-detection algorithm to the data to outline edges of items imaged in the x-ray data. In some implementations, the item may be identified by aggregating pixels having similar or the same effective atomic number into clusters and identifying boundaries between clusters as boundaries of the item. Some of the pixels in the region are correlated with the item such that the item is associated with an effective atomic number (540). The pixels in the region that are located within or on the boundary of the item are correlated with the item. Because the pixels are each associated with an effective atomic energy number, the item is associated with the effective atomic energy number of the pixels. In some examples, the item may be composed of more than one material, and the materials may have different effective atomic numbers. For example, a homemade bomb may include plastic explosives and a metal detonator, and the plastic explosives and the metal detonator have different effective atomic numbers. Thus, in these examples, the item includes pixels having different effective atomic numbers, and the item is not associated with one effective atomic number.

An image of the item is rendered (550). In the rendered image, the item has a display style that is based on the effective atomic number of the item. For example, the display style may be color, and, in these examples, the rendered image is a color-coded image of the item. For example, a metallic item may have a display style of blue in a color-coded image. In other examples, the display style may be a pattern, such as shading or cross-hatching, or the display style may be a texture. In some examples, the display style may be more than one of color, texture, and a pattern. In examples in which the display style is a pattern, a metallic item may, for example, have a display style of dots. Some examples may have a display style that combines color and patterns. In some examples, a second item may be identified, and a range of effective atomic numbers of interest may be received. The second item may overlap, or cover the identified item. For example, the identified item may be a plastic item, and the second item may be a piece of sheet metal partially covering the plastic item. The overlapping area where the second item covers the plastic item may be referred to as the region of overlap. Rather than being represented as an average or composite of the effective atomic numbers of the plastic item and the sheet metal, the region of overlap may have the display style of either the display style of the plastic item or the display style of the sheet metal. In particular, the region of overlap has the display style of the sheet metal if the effective atomic number of the sheet metal is in the range of effective atomic numbers of interest, and the region of overlap has the display style of the plastic item if the effective atomic number of the plastic item is within the range of effective atomic numbers of interest. In some implementations, the display style may be a texture, cross-hatching, and/or shading in addition to, or instead of, color.

Figure 6A:
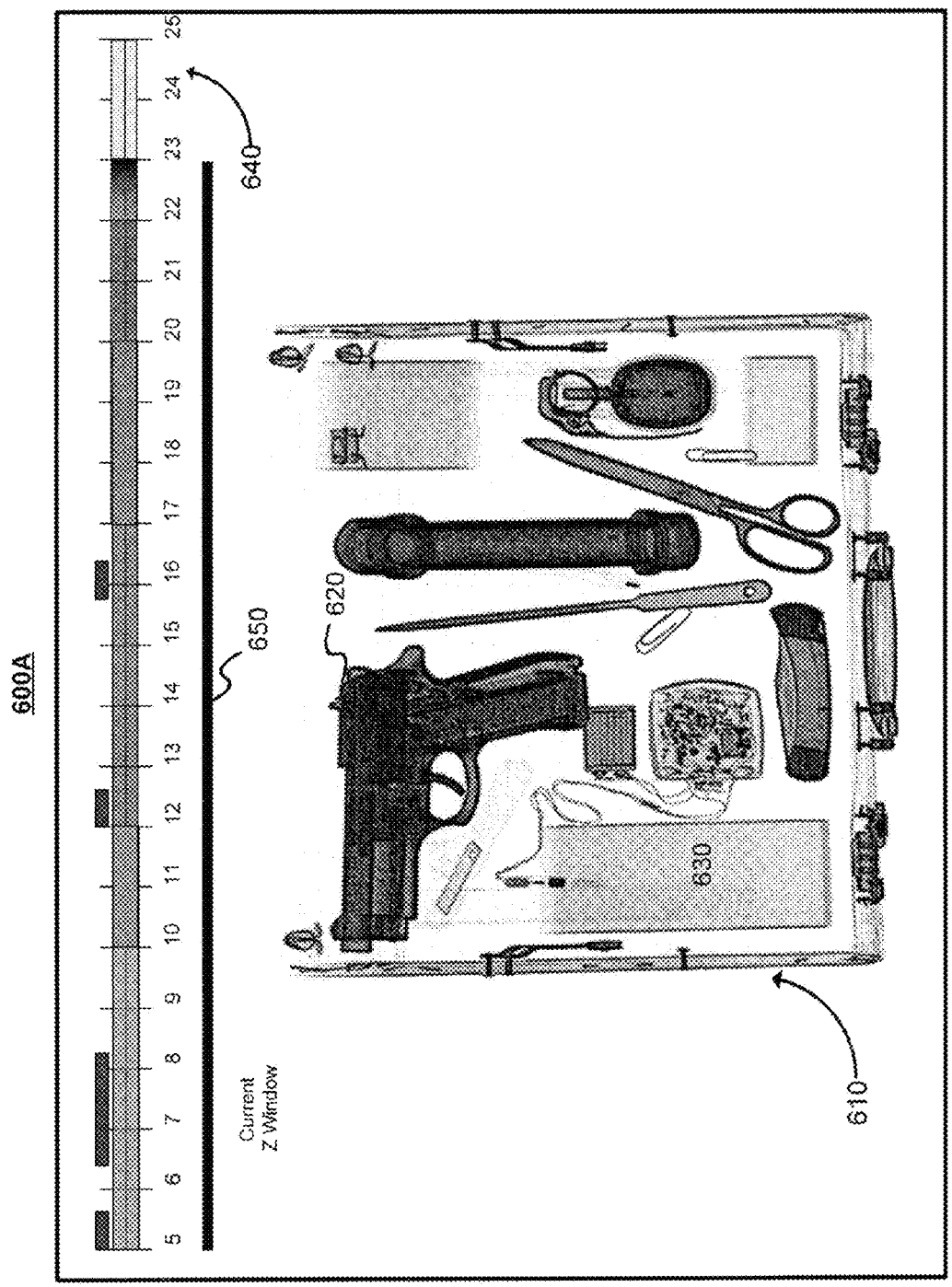
FIGS. 6A-6C show example images of materials in effective atomic number space.

Referring to FIG. 6A, an example image 600A shows an image of a suitcase 610 and the contents of the suitcase 610, including a metal gun 620 and a plastic item 630 that is constructed from metal and cloth and enclosing metal materials. The image 600A is in effective atomic number space and is color-coded according to a legend 640. The image 600A includes those effective atomic numbers that are included in a range specified by a selector 650. In the example shown in FIG. 6A, the selector 650 indicates that atomic numbers five to twenty-three are included in the image 600A. A selection of a range of effective atomic numbers of interest may be received based on the size and/or position of the selector 650.

Figure 6B:
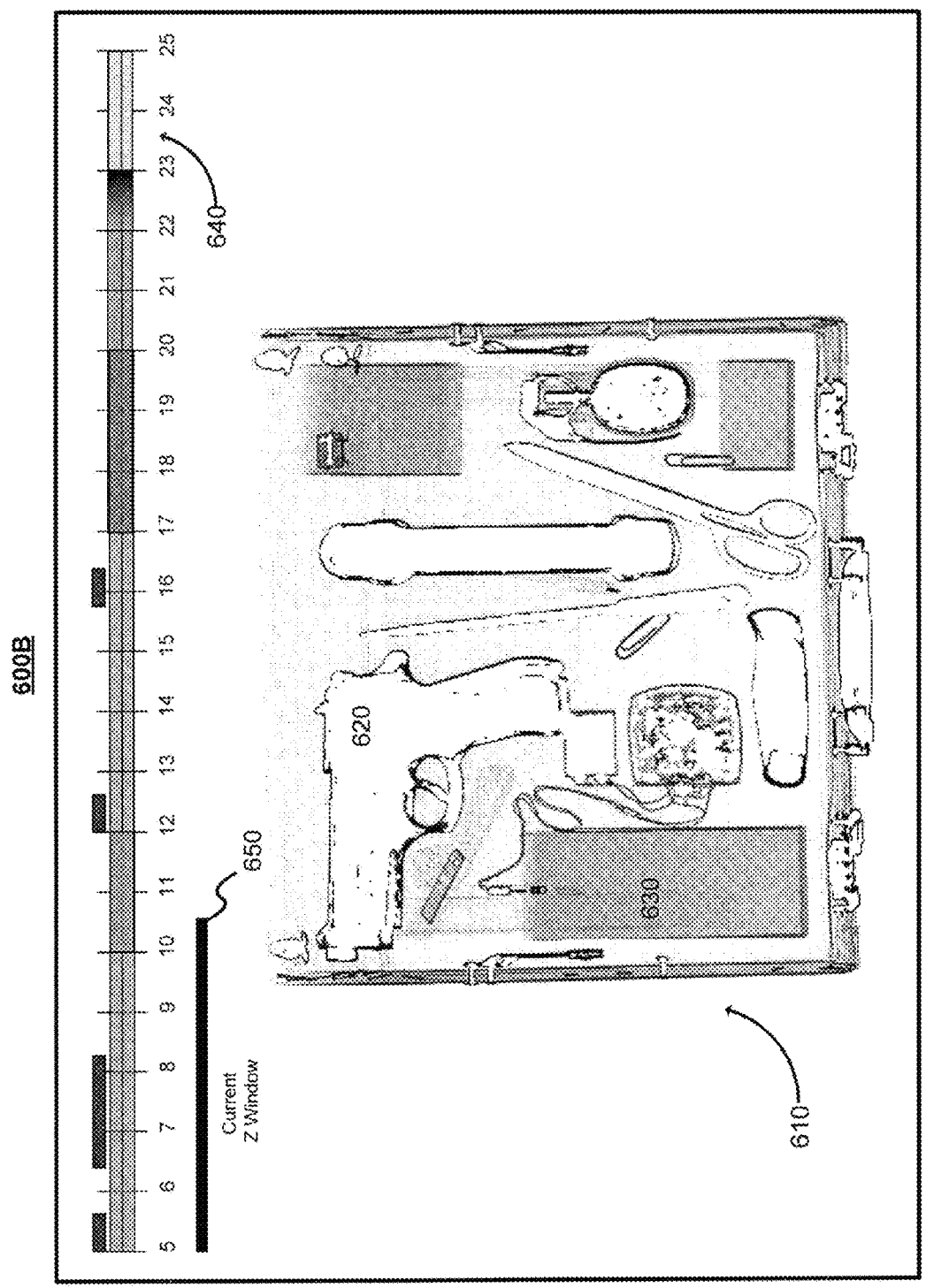
Figure 6C:
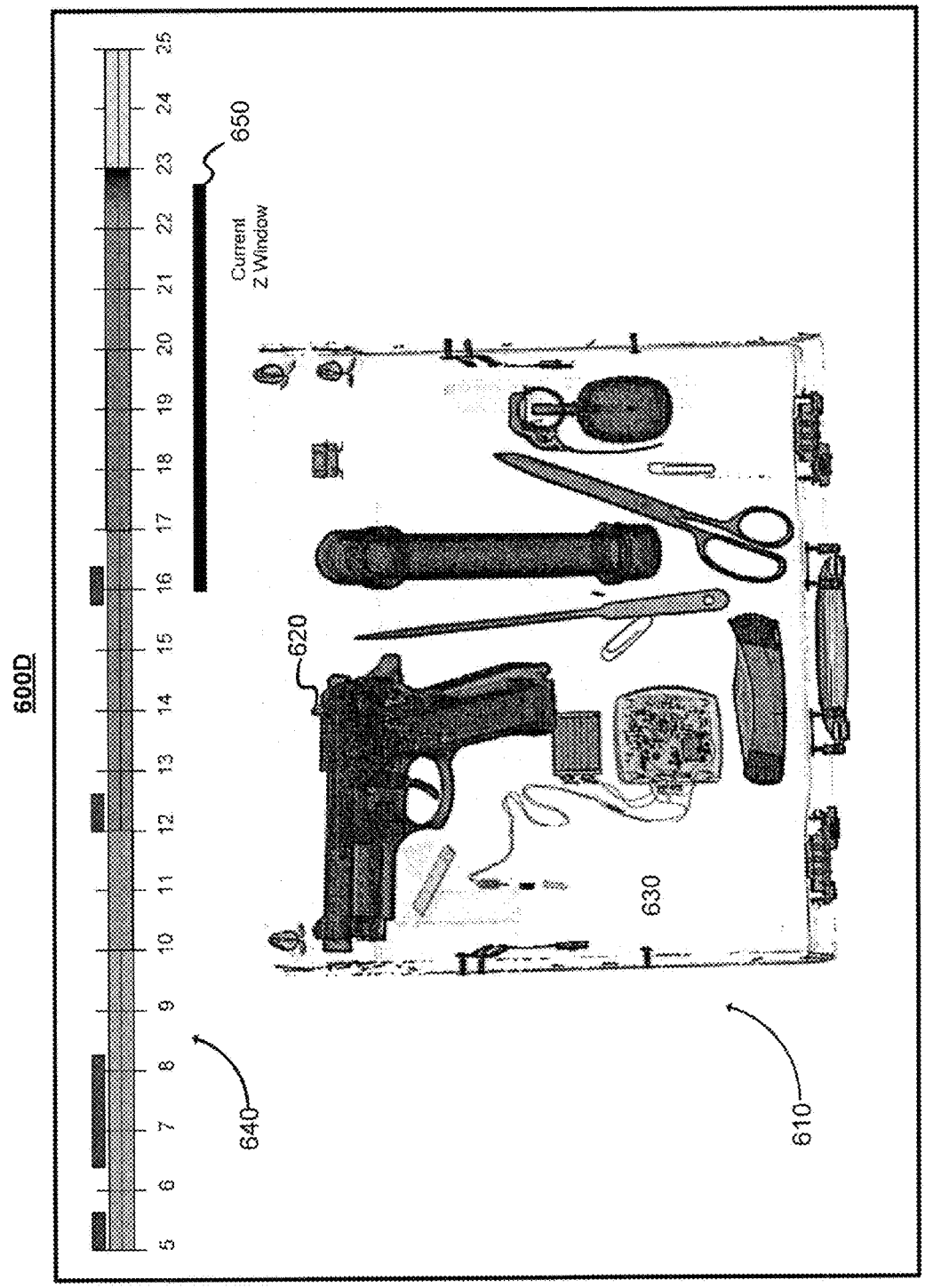

Referring to FIG. 6B, the selector 650 is re-sized and re-positioned such that the window of atomic numbers of interest is between 5 and about 10.5. Thus, a window of effective atomic numbers between 5 and about 10.5 is received in this example. The color coded-image of the materials associated with the object of interest is updated such that the updated image includes the selected effective atomic numbers of interest. Continuing with the example shown in FIG. 6B, the image 600A is updated to an image 600B that includes effective atomic numbers between 5 and 10.5. As a result, the metal objects, such as the gun 620, which have effective atomic numbers beyond the selected range, are de-emphasized. The non-metallic objects, such as the item 630, become more prominent. Referring to FIG. 6C, the selector 650 is re-sized and repositioned such that the selector 650 indicates that effective atomic numbers between 16 and 23 are included in an updated image 610C. In some implementations, a histogram (not shown) of effective atomic numbers included in the image may be displayed. The histogram represents the percentage of pixels in the image at each of the effective atomic numbers shown in the legend 640.

A number of implementations have been described. Nevertheless, it will be understood that various modifications may be made without departing from the scope of the disclosure. Accordingly, other implementations are within the scope of the following claims.

What is claimed is:

1. A system comprising:
 a processor configured to:
  receive effective atomic numbers associated with pixels in a region,
  identify a first item within the region and a second item within the region,
  correlate at least one of the pixels in the region with the first item such that the first item is associated with a first effective atomic number, and
  correlate at least one of the pixels in the region with the second item such that the second item is associated with a second effective atomic number; and
 a display configured to render an image of the region, the at least one pixel of the first item having a first display style associated with the first effective atomic number and the at least one pixel of the second item having a second display style associated with the second effective atomic number.

2. The system of claim 1, wherein the first item comprises a single pixel, and the second item comprises a single pixel.

3. The system of claim 1, wherein the first item comprises a group of pixels.

4. The system of claim 3, wherein the first item covers at least part of the second item.

5. The system of claim 1, further comprising an opening to the region.

6. The system of claim 5, wherein the opening is configured to receive a cargo carried by a motorized vehicle.

7. The system of claim 1, wherein the display is a touch screen.

8. The system of claim 1, wherein the first item covers at least part of a third item.

9. The system of claim 1, further comprising:
 a source of penetrating radiation that is directed towards the region; and
 a sensor configured to detect the penetrating radiation.

10. The system of claim 9, wherein the penetrating region comprises x-rays of at least two energies.

11. A method comprising:
- receiving effective atomic numbers associated with pixels in a region;
- identifying a first item within the region and a second item within the region;
- correlating at least one of the pixels in the region with the first item such that the first item is associated with a first effective atomic number;
- correlating at least one of the pixels in the region with the second item such that the second item is associated with a second effective atomic number; and
- presenting an image of the region, the at least one pixel of the first item having a first display style associated with the first effective atomic number and the at least one pixel of the second item having a second display style associated with the second effective atomic number.

12. The method of claim 11, wherein the first display style comprises a color, and the second display style comprises a color different from the color of the first display style.

13. The method of claim 11, further comprising identifying a third item, the third item being associated with a third effective atomic number that is lower than the second effective atomic number, and the third item being at least partially covered by the second item.

14. The method of claim 13, wherein the image presented of the region comprises a representation of the entire third item.

15. The method of claim 13, further comprising receiving an indication of a range of effective atomic numbers of interest.

16. The method of claim 15, wherein the image presented includes only representations of items that are associated with an effective atomic number that is within the indicated range.

17. The method of claim 11, wherein identifying the first item within the region comprises identifying a single pixel within the region, and wherein identifying the second item within the region comprises identifying a single pixel within the region.

18. The method of claim 11, further comprising accessing penetrating spectral data for the region, and wherein identifying the first item within the region and identifying the second item within the region comprises identifying the first and second items in the penetrating spectral data.

19. The method of claim 11, further comprising presenting an interactive interface for manipulating at least one visual feature of the image of the region.

20. A computer program product tangibly embodied on a non-transitory computer-readable medium, the computer program including instructions that, when executed, cause a processor to perform operations comprising:
- receiving effective atomic numbers associated with pixels in a region;
- identifying a first item within the region and a second item within the region;
- correlating at least one of the pixels in the region with the first item such that the first item is associated with a first effective atomic number;
- correlating at least one of the pixels in the region with the second item such that the second item is associated with a second effective atomic number; and
- presenting an image of the region, the at least one pixel of the first item having a first display style associated with the first effective atomic number and the at least one pixel of the second item having a second display style associated with the second effective atomic number.

* * * * *